US007233012B2

(12) United States Patent
Zyromski et al.

(10) Patent No.: US 7,233,012 B2
(45) Date of Patent: Jun. 19, 2007

(54) FLEXIBLE RADIATION SOURCE AND COMPACT STORAGE AND SHIELDING CONTAINER

(75) Inventors: Kristiana E. Zyromski, Frazier Park, CA (US); Franklin B. Yeager, Woodland Hills, CA (US); Joseph David Hathcock, Huntington Beach, CA (US); Jeffrey James Kempton, Burbank, CA (US)

(73) Assignee: Eckert & Ziegler Isotope Products, Inc., Valencia, CA (US)

( * ) Notice: Subject to any disclaimer, the term of this patent is extended or adjusted under 35 U.S.C. 154(b) by 567 days.

(21) Appl. No.: 10/872,084

(22) Filed: Jun. 18, 2004

(65) Prior Publication Data

US 2004/0256580 A1 Dec. 23, 2004

Related U.S. Application Data

(60) Provisional application No. 60/479,656, filed on Jun. 18, 2003.

(51) Int. Cl.
*G21G 4/06* (2006.01)
*A61N 5/00* (2006.01)

(52) U.S. Cl. ................................ 250/493.1; 250/496.1; 250/522.1; 250/519.1

(58) Field of Classification Search ..................... None
See application file for complete search history.

(56) References Cited

U.S. PATENT DOCUMENTS 6,770,019 B1 * 8/2004 Fritz et al. ..................... 600/3

* cited by examiner

*Primary Examiner*—Nikita Wells
(74) *Attorney, Agent, or Firm*—Christie, Parker & Hale, LLP

(57) ABSTRACT

A flexible radiation source. The flexible radiation source has a layer of flexible material with at least one radionuclide dispersed therein to form a flexible, radioactive matrix. A layer of flexible nonradioactive material is also provided to which the flexible, radioactive matrix is permanently attached. The flexible radiation source can be folded or rolled from an extended or planar configuration to a folded or rolled configuration without causing the at least one radionuclide from becoming separated therefrom. The flexible matrix material is free from encapsulation by any rigid structure when in use. A storage and shielding container with a compact form factor is provided. The form factor of the storage and shielding container accommodates the flexible radiation source when the flexible radiation source is in its rolled or folded configuration, but does not accommodate the flexible radiation source when it is in fully extended or planar configuration.

107 Claims, 10 Drawing Sheets

FLEXIBLE RADIATION SOURCE AND COMPACT STORAGE AND SHIELDING CONTAINER

CROSS-REFERENCE TO RELATED APPLICATION(S)

This application claims priority from U.S. Provisional Application No. 60/479,656, filed Jun. 18, 2003.

BACKGROUND OF THE INVENTION

Nuclear medicine cameras, which include gamma cameras, Anger cameras and SPECT cameras (SPECT being an acronym for single photon emission computed tomography), must be regularly calibrated to ensure accurate performance. The field of view of a gamma camera is comprised of many pixels, each pixel being determined by a combination of a scintillation detector and photomultiplier tube, or other device to convert incident radiation into electronic signal, and subsequent signal-processing electronics. The pixels of a gamma camera may have inherent differences in response and performance, or "nonuniformity", since they are dependent on discrete devices, and so they must be normalized to one another such that the same intensity of radiation presented to any pixel of the camera will result in the same intensity of signal (or "counts") in the corresponding pixel of the final image. This calibration is normally performed using a radiation source which presents a uniform field to all pixels of the camera, said source being commonly known as a "flood source" or "sheet source".

Current flood sources are generally made of a cast epoxy with a radionuclide or radionuclides evenly dispersed throughout, with this "active element" encased in a rigid plastic housing. These flood sources typically have a weight averaging from about 3.1 kg to 5.5 kg (7 to 12 lbs), depending on manufacturer and model, and the manufacturer generally provides a shielded storage case with rigid sides and a lining of lead or other high-density, high-atomic-number material to block radiation from the source. Storage cases of this style can weigh in excess of 31 kg (70 lbs), and are commonly about 61 cm to 91 cm (2 to 3 feet) high and about 61 cm (2 feet) or more wide by about 7.6 cm to 12.7 cm (3 to 5 inches) thick, to accommodate the rigid flood source. Being tall and excessively heavy for routine carrying, this style of case typically has wheels at the bottom so they may be moved from place to place. Even with wheels, these cases are cumbersome and awkward to ship, handle and move around.

Kalas et al., (US Patent application No. US 20020185613 A1) discloses a method of producing flood sources in which the radionuclide is deposited on the surface of a thin, lightweight substrate and fixed to seal the radionuclide. This "active element" is then encased in an outer housing which is sufficiently rigid to allow for fixed positioning during gamma camera calibration, in order to present a uniform radiation field to the camera. Currently available flood sources of this style have a weight of approximately 1.4 kg (3 lbs), which is more convenient to handle than the heavier cast-epoxy style sources described previously. In Kalas et al., it is disclosed that the thin substrate may be made of a flexible material such as paper, which can be removed from the rigid outer housing and folded or rolled for easier shipment or disposal. However, this style of flood source still requires the rigid outer housing to fix the active element's position in a flat configuration during gamma camera calibration, in order to present a uniform radiation field to the camera. Horst and Menuhr (U.S. Patent Application 20030104178) discuss a method of producing a flood source by printing a radioactive solution on a substrate; including a method of recycling the flood source active element by reprinting on the substrate after the original radioactive printing has decayed. A disadvantage of the methods of Kalas et al., and of Horst and Menuhr is that said methods are based on deposition of the radioactive material on the surface of a substrate. If such a substrate is then flexed, rolled, or folded, the radioactive deposition can develop creasing, cracking, flaking, or other inhomogeneities which render the source unusable for the purpose of gamma camera calibration. Such cracking or flaking may also allow release or dispersion of the radioactivity, contaminating the environment in which it is being used. For these reasons currently available flood sources produced by substrate-deposition methods are encased in a rigid outer encapsulation. In addition to providing a flat geometry of the active element, this rigid capsule protects the active element from creasing, flaking, and otherwise developing structural flaws through repeated handling. Currently available flood sources of this style are generally provided with a rigid-sided shielded storage case of the type described above, and so although the flood source is more convenient to handle than the heavier cast-epoxy style sources, the case remains large, heavy, and unwieldy.

O'Kane et al., (US Patent Application No. 20020060300 A1) discloses a soft-sided shielded storage and transport bag for flood sources, which has a form factor conforming more closely to the dimensions of the flood source, allowing the shielded bag to be of a lighter weight than the hard-sided wheeled cases described above. The latest currently commercially-available version of this shielded bag weighs approximately 14 kg (30 lb), and is manufactured with handles in order that the bag may be carried. An unshielded wheeled case for storage and transport of the bag is an option offered by the manufacturer for users not wishing to carry the about 14 kg (30-lb) bag by the handles.

The dimensions of the active element of a flood source and the level of radioactivity of the source are dictated by the dimensions and specifications of the gamma camera the source is designed to calibrate. In order to provide adequate shielding of the source when not in use, a minimum thickness of shielding material must be used. Since the inner dimensions of the shielding case are dictated by the dimensions of the flood source it is designed to contain, then clearly, for a flood source of given dimensions in a rigid capsule, there is a lower limit to the weight of the shielding case below which said case will not provide shielding adequate for protection of the user when the source is placed in the case.

It accordingly would be desirable to provide flood sources in flexible form factors that can be folded, rolled, etc., to reduce their deployed outer dimensions to a smaller size so that the size and weight of the shielding container can also be reduced. It would also be desirable to provide a radioactive source that can be used when oriented not only on a plane, but also on curved and other non-planar orientations. This flexible radiation source should be durable when flexed, rolled, or folded in order to maintain the integrity and original distribution of radioactivity despite repeated handling.

SUMMARY OF THE INVENTION

The present invention provides a flood source which is flexible, yet does not require a rigid outer encapsulation to fix the active element in a flat configuration during gamma camera calibration or to protect the active element from direct handling. The flood source may be provided with a flexible outer encapsulation to allow the source to be routinely rolled or folded for placement in a shielded storage case with a small form factor. By geometry, the shielded storage case requires less shielding material, thus providing equivalent or better shielding than current cases for rigid-capsule flood sources at a fraction of the weight. There are certain situations in which it is desirable to support the flood source by less than the full area of the source, and for such situations the flexible flood source may be provided with a support frame or plate. This frame or plate may be integral to the flood source or detachable for separate storage, and the frame or plate may be designed to provide a rigid support for the flexible flood source in "extended" configuration, and roll or fold into a compact shape for storage in "collapsed" configuration. The flood sources can be used for testing and calibrating gamma cameras, as well as for other uses in a flat configuration. The flood sources can also be used for non-flat planar configuration applications, such as for contact with curved surfaces, e.g. pipes, hulls, etc., for use in measuring the integrity of the curved walls thereof.

BRIEF DESCRIPTION OF THE DRAWINGS

The invention can be more readily understood by referring to the accompanying drawing, as follows.

DETAILED DESCRIPTION OF THE INVENTION

Figure 1:
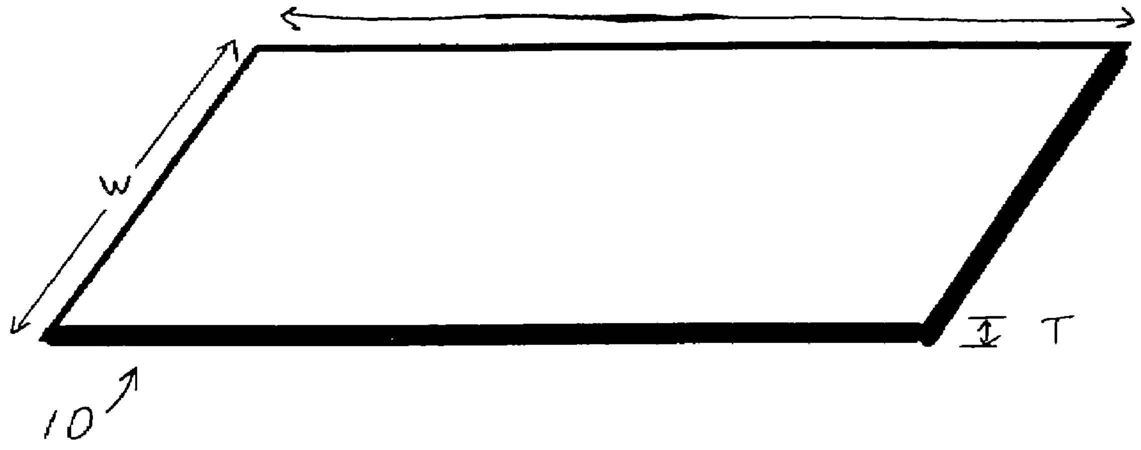
FIG. 1 is a perspective view showing an exemplary flexible flood source of the invention having a generally rectangular shape in its planar orientation.

The invention is a radiation source comprised of a radionuclide dispersed throughout a flexible matrix (the flexible "active element"). The flexible matrix may be thick enough to independently maintain its integrity, or may be a thin matrix of flexible material applied to a flexible nonradioactive material provided for structural integrity, and permanently incorporated therein. (If provided, this flexible non-radioactive material is considered an integral part of the "flexible matrix".) The radionuclide comprises a known calibrator for the detector system with which the source is used, or has radiation energies similar to radionuclides used with this detector system. These radionuclides include, but are not limited to Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, with Ba-133, Co-57, Ge-68, Na-22, Gd-153, Cs-137, and Se-75 being particularly good nuclides. Furthermore, combinations of two or more radionuclides can be used in the active element.

The level of radioactivity of the active element may range from about 10 nanocuries or lower to about 100 millicuries or higher, depending on the radionuclide chosen and the requirements of the conditions of use. The radioactivity may be dispersed uniformly throughout the flexible matrix, providing a uniform field from the active area, or it may be dispersed non-uniformly, only through portions of the flexible matrix, providing regions of activity and nonradioactive or less radioactive regions.

The radionuclide may be dispersed throughout the active area(s) of the flexible matrix by physical methods (suspension) or chemical methods (dissolution), depending on the chemical form of the radionuclide used and on the physical and chemical properties of the constituent components of the flexible matrix material.

The flexible matrix material should have sufficient durability to allow for repeated rolling and unrolling or folding and unfolding (preferably in excess of 100 cycles) without cracking, tearing, or otherwise compromising the integrity of the active element. The flexible matrix material should have sufficient radiation resistance to withstand the radiation field emitted by the radionuclide over the working life of the source, without cracking, becoming brittle, or otherwise compromising the integrity of the active element.

The flexible matrix material can be an epoxy, a urethane, a silicone, a rubber, a flexible plastic, a cellulose, a polymer gel, a flexible metal sheet or some other flexible material, or a combination of two or more of these materials.

The active element may be made to have sufficient weight and/or polymer "memory" such that it will lie flat when placed on a flat surface such as a gamma camera head, without the necessity of a rigid encapsulation. The material from which the flexible radiation source is made can be made from memory material that will assume the geometry in which the flexible source material was made (e.g. generally flat, curved, etc.)

The active element may range in size from about 12.7 cm×12.7 cm (5"×5") to about 76 cm×76 cm (30"×30"), with thickness sufficient to provide the necessary durability as dictated by the matrix material chosen, but typically about 0.4 mm to about 3.8 cm (1/64" to 1.5"). Depending on the matrix material and size dimensions, the active element may weigh from about 0.04 kg or less to about 3.6 kg or more (0.1 lb. to 8 lbs).

Turning now to the specific exemplary embodiments of invention, FIG. 1 is a perspective view showing an exemplary flexible flood source 10 of the invention in its planar orientation. It has a generally rectangular shape of length L, width W and thickness T. The total outer surface area will thus be roughly equal to T(2L+2W)+2(L×W). If flood source 10 were to be stored in a storage and shielding container (not shown) in its planar orientation, such as would be required if the flood source were a conventional, rigid flood source, the container would need to have internal dimensions at least as large as L×W×T, and a radioactive shielding surface area that is larger than to T(2L+2W)+2 (L×W) and with a shielding thickness chosen as is required. Since radioactive shielding material tends to be relatively heavy, this can result in conventional, planar flood source storage and shielding container being quite heavy.

Figure 2:
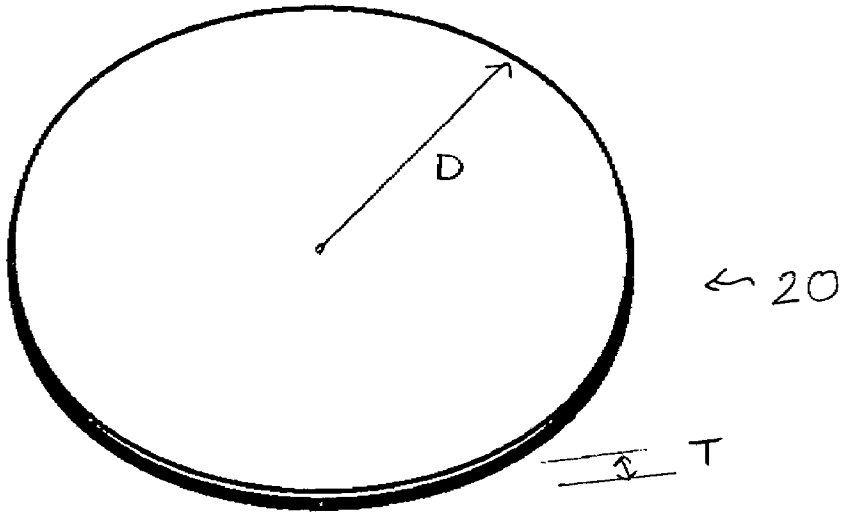
FIG. 2 is a perspective view showing an exemplary flexible flood source of the invention having a generally circular shape in its planar orientation.

FIG. 2 is a perspective view showing an exemplary flexible flood source 20 of the invention having a generally circular shape in its planar orientation with a diameter D and thickness T.

Figure 3:
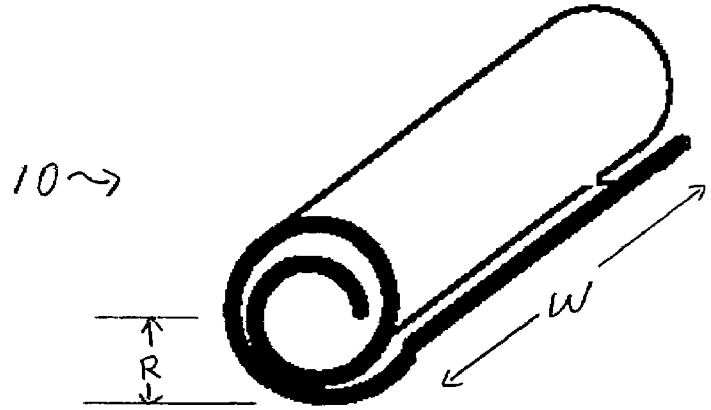
FIG. 3 is a perspective view showing an exemplary flexible flood source of FIG. 1 in its rolled up orientation.

FIG. 3 is a perspective view showing an exemplary rectangular flexible flood source 10 of FIG. 1 rolled up along its length L, so that it forms a generally roll shaped object with a radius of R and width W. In the rolled up orientation of FIG. 3, the total outside surface area of the object is reduced from the planar size of about to T(2L+2W)+2(L×W) to about $W2\pi R+2\pi R^2$, which for small radiuses R can result in substantially smaller outwardly facing surface areas of the rolled up flood source compared to the same flood source in its planar orientation.

Figure 4:
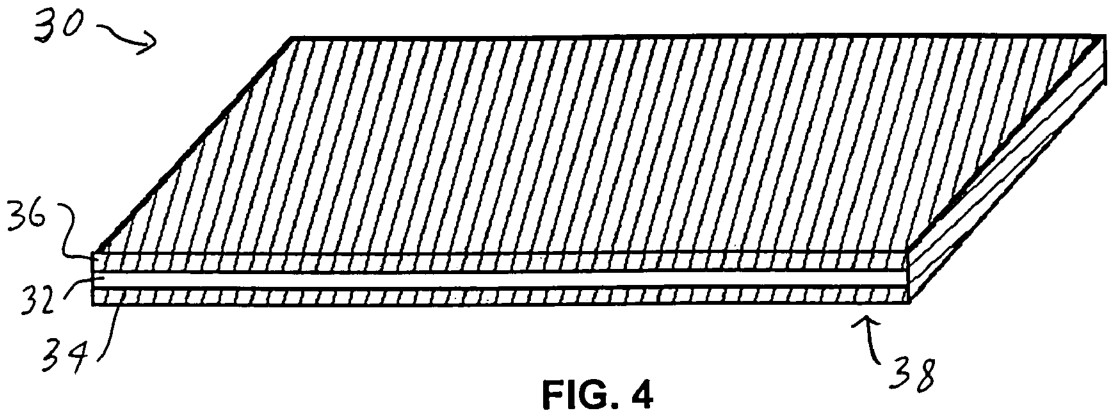
FIG. 4 is a perspective view showing an exemplary flexible flood source of the invention wherein a radiation source is integrally encapsulated in a flexible matrix.

FIG. 4 is a perspective view showing an exemplary flexible flood source 30 of the invention wherein a radiation source layer 32 is integrally encapsulated in a flexible matrix between non-radiation source layers 34 and 36. Although the facing leading edge 38 reveals the edge of radiation source layer 32, in actual construction, the non-radiation source layers 34 and 36 can be made to intersect and cover the outside edges of radiation source layer 32 (not shown.) The flexible encapsulation may be a flexible coating applied directly to the active element, such as a nonradioactive layer of the flexible matrix material of the active element, or can be a separate layer attached thereto.

Figure 5:
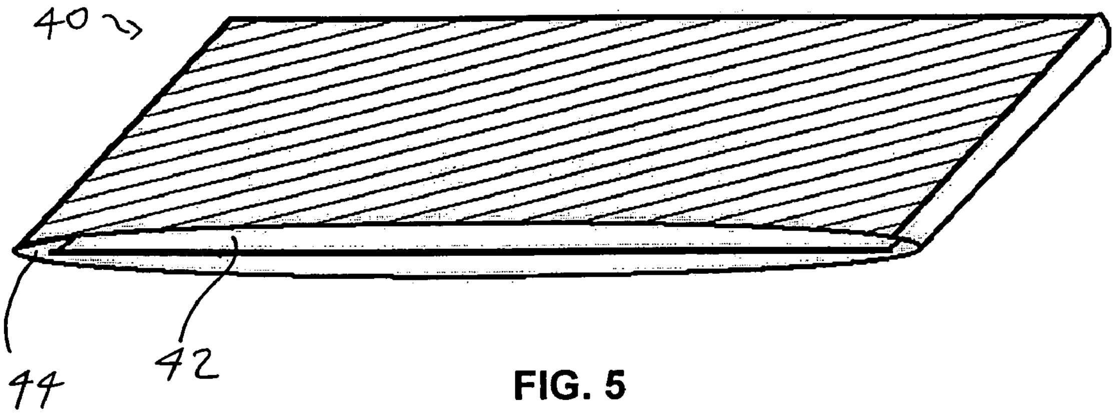
FIG. 5 is a perspective view showing an exemplary flexible flood source of the invention wherein a radiation source is on a separate element, which is retained within a flexible encapsulating cover.

FIG. 5 is a perspective view showing an exemplary flexible flood source 40 of the invention wherein a radiation source is a separate, flexible active element 42 that is retained within a flexible, encapsulating cover 44. Encapsulating cover 44 can either be made to be permanently sealed shut (e.g. by sewing, bonding, or fusing at the open edges to form a sealed encapsulation around the flexible element 42), or can be made to be openable so that the separate, flexible active element 42 can be accessed, e.g. for servicing, renewal, etc. The flexible encapsulating cover may be made of a flexible material such as fabric or flexible plastic sheet, which is sized to the approximate extended dimensions of the flexible active element 42.

Figure 6:
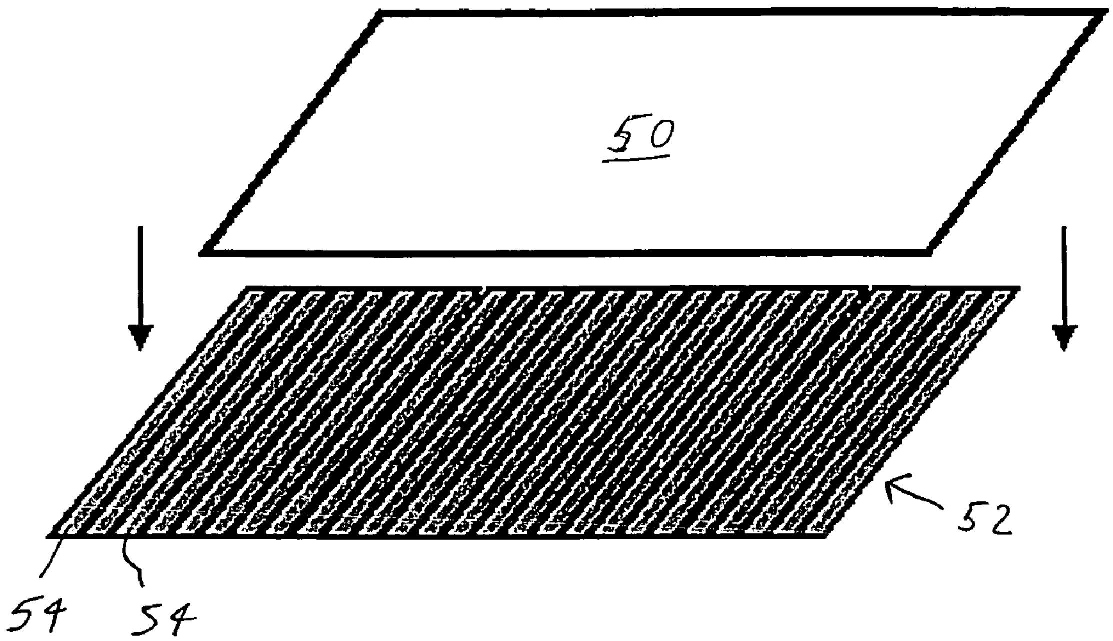
FIG. 6 is a perspective view showing an exemplary flexible flood source and a support plate of the invention in their planar modes.

FIG. 6 is a perspective view showing an exemplary flexible flood source 50 of the invention and a support structure or plate 52 (having a series of segments or slats 54) in their planar modes, with flexible flood source 50 lifted up above support plate 52.

Figure 7:
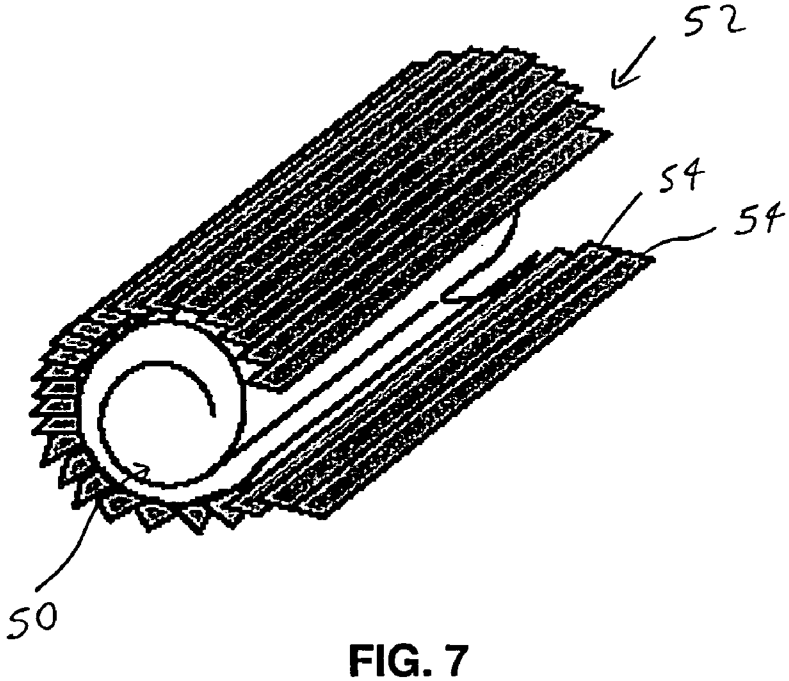
FIG. 7 is a perspective view showing the exemplary flexible flood source and its support plate of FIG. 6 in their rolled up mode.
Figure 8:
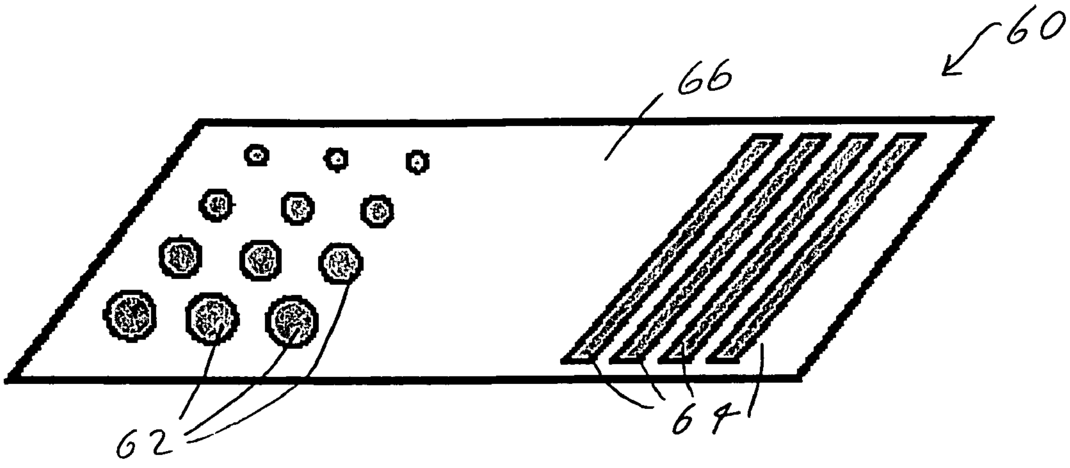
FIG. 8 is a perspective view showing an exemplary flexible flood source having radiopaque or non-radioactive patterns formed on a hot background.

FIG. 7 is a perspective view showing the exemplary flexible flood source 50 and its support plate 52 of FIG. 6 in their rolled up mode, with support plate 52 being rolled around flexible flood source 50. Support plate 52 can comprise a series of segments or slats 54 that when slid together, form a generally rigid plate (as shown in FIG. 6), and when slid apart (as shown in FIG. 7), permit the support plate to be rolled or folded. The construction of the support plate can be varied as desired, and other constructions are contemplated. The segments or slats 54, which are adapted to connect or interlock to provide a flat, rigid support configuration, and which, when not connected or interlocked permit the support plate to be flexed, rolled, or folded. The segments or slats 54 can be made such that when the support plate is in its support configuration, the support plate has generally uniform transparency to radiation over a surface which supports the flexible matrix material. Alternately, the segments or slats 54 can have areas of differing transparency to radiation, or radiopaque properties. The support plate 52 can be made of a lightweight, low-atomic-number material. The support plate can be made of materials such as thermoplastics, epoxy resins, fiberglass, wood or wood-fiber products, carbon-fibers, and composites thereof. FIG. 8 is a perspective view showing an exemplary flexible flood source 60 having radiopaque or non-radioactive patterns 62 and 64 with a radioactive background 66. The patterns 62 and 64 can also have a level of radioactivity lower than that of the radioactive background 66. The radiopaque material preferably comprises an element or composite material with a density greater than 5 g/cc. Elements that fit this definition include high-density, high-atomic-number material that include, but are not limited to lead, tungsten, bismuth, copper, cobalt, gold, nickel, silver, tantalum, and alloys, compounds, composites based on these materials, and combinations thereof. With tungsten and tungsten-based alloys, compounds, and composites being the most favorable choice; and lead and lead-based alloys, compounds, and composites being the second most favorable choice. It has been found that good performance can be achieved if the radiopaque material comprises at least 10% by weight of at least one element with an atomic number greater than 20.

For example, the radiopaque material can comprise at least 10% by weight of at least one of lead, tungsten, tantalum, bismuth, uranium, and combinations thereof.

Figure 9:
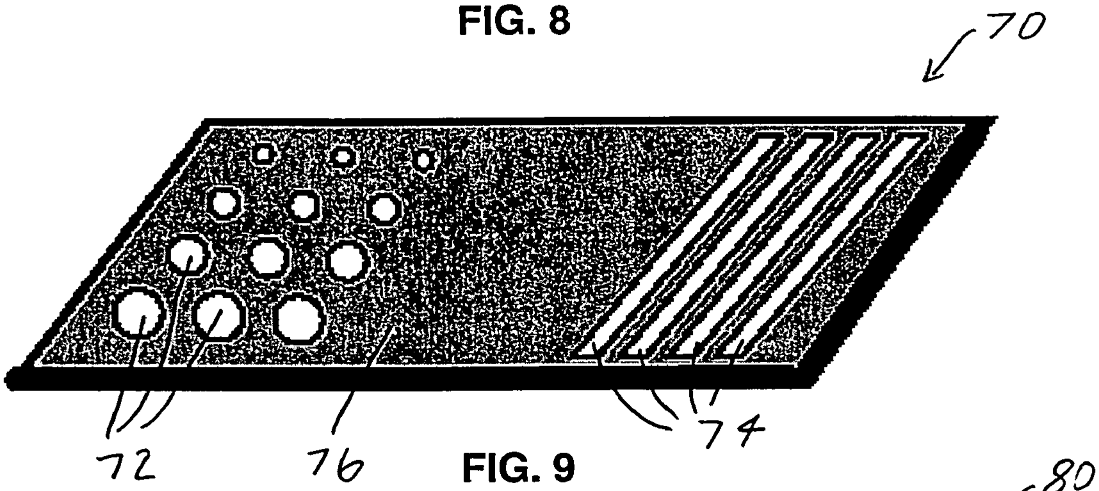
FIG. 9 is a perspective view showing an exemplary flexible flood source having radiopaque or non-radioactive background with hot patterns.

FIG. 9 is a perspective view showing an exemplary flexible flood source 70 having radioactive patterns 72 and 74 with a radiopaque or non-radioactive (or lower level of radioactivity) background 76. In FIGS. 8 and 9, the radiopaque or non-radioactive patterns 62 and 64, and 72 and 74, respectively, can comprise circles and stripes (or any other desired shapes) of a given widths, diameters and spacings (about 0.5 mm to 5 cm) to measure the resolution of the gamma camera. The levels of activity of the circles and/or stripes 72 and 74 or the background 66 may vary, in order to check camera response to various activity levels and the radiopaque materials can be formed of conventional high density atomic number materials.

Figure 10:
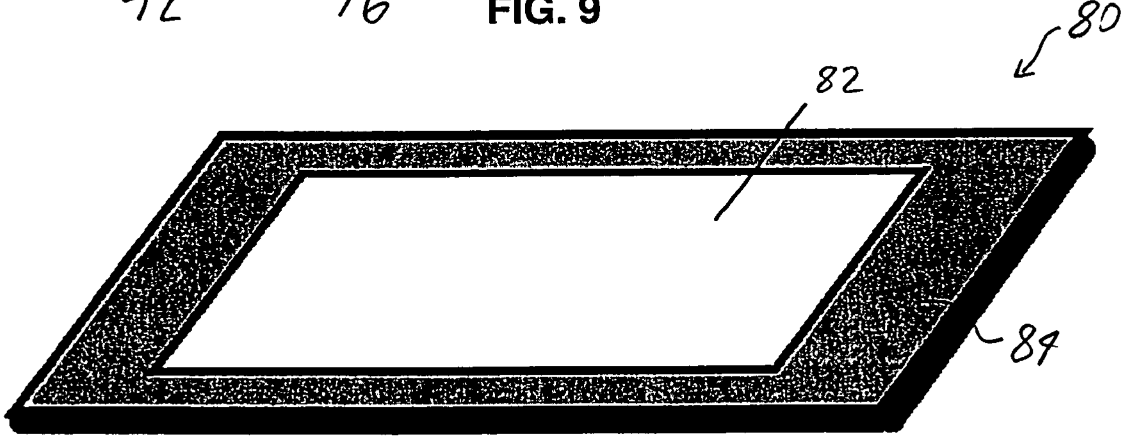
FIG. 10 is a perspective view showing an exemplary flexible flood source having a radioactive central region and radiopaque or non-radioactive edges.

FIG. 10 is a perspective view showing an exemplary flexible flood source 80 having a radioactive central region 82 and radiopaque or non-radioactive edges 84. The radiopaque edges 84 can provide convenient places for a user to handle the flexible flood source 80 to minimize close contact with radioactive materials. Alternately, if desired, a smaller sized active element can be placed in a larger encapsulation to create "cold" perimeters areas around the "hot" area.

The flexible flood source may be provided with other rigid support frames or plates for use in applications in which it is desirable to support the flexible source by less than the full area of the source. This support may take the configuration of a frame which attaches to the edges of the source (see FIGS. 11 and 13); a frame with additional supports extending across the face of the source, or a solid plate which supports the entire face of the source (not shown). This support may also be made of multiple attached sections, which provide a flat support in extended configuration, but which can fold, collapse, or roll into a compact geometry for storage. (See FIGS. 6 and 7.) In the instance in which the support takes the configuration of a plate which supports the entire face of the source, the plate may have interlocking segments in order to provide a uniform thickness of material to ensure uniform attenuation of the radiation passing through the plate, without spaces, cracks, or regions of increased or decreased thickness which would affect the uniformity of the radiation field through the support.

The supports may also be integrated or attached permanently to the flexible active element or to the flexible encapsulation, or it may be detachable for separate use and storage. If desired, the supports may be made of a lightweight, low-atomic-number material in order to be reasonably translucent to gamma radiation; the material may consist of but is not limited to thermoplastic, epoxy resin, fiberglass, aluminum, or wood or wood-fiber-based products. The material may be reinforced with carbon, glass, or other fiber for added rigidity and/or may comprise composite materials.

Figure 11:
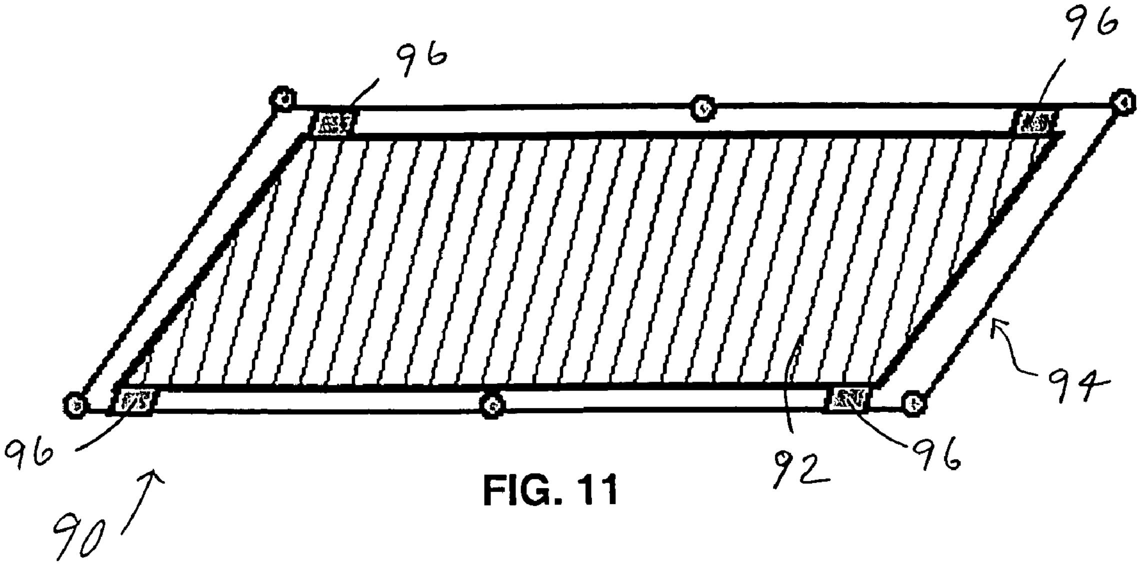
FIG. 11 is a perspective view showing an exemplary flexible flood source and an exemplary collapsible frame in their deployed state so that the flexible flood source is extended to a flat orientation.

FIG. 11 is a perspective view showing an exemplary combination flexible flood source and collapsible frame 90, with an exemplary flexible flood source 92 being detachably attached to a collapsible frame 94 with attachments 96.

Figure 12:
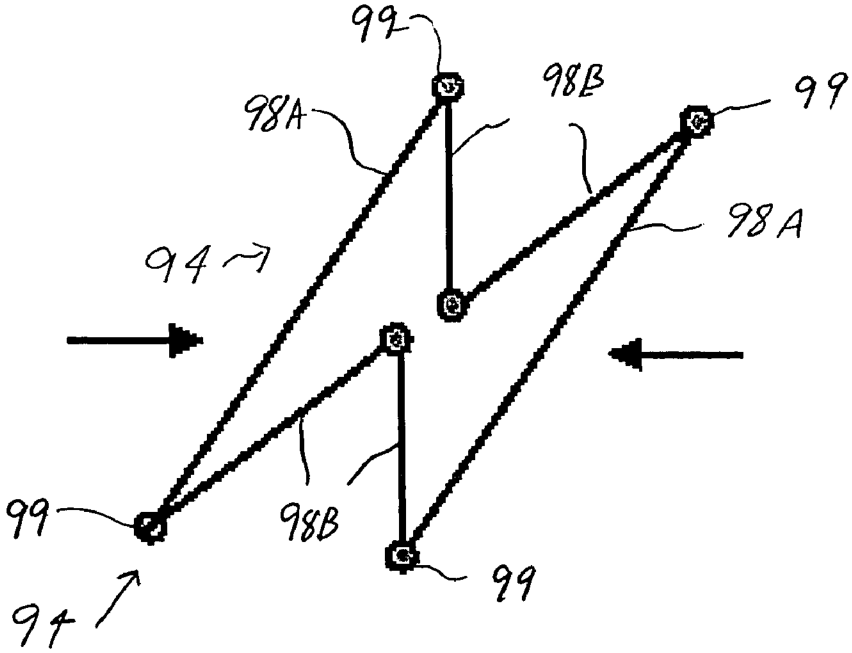
FIG. 12 is a perspective view showing the exemplary collapsible frame of FIG. 11 in its partially collapsed state.

FIG. 12 is a perspective view showing the exemplary collapsible frame 94 of FIG. 11, but in its collapsed state with flexible flood source 92 removed. Collapsible frame 94 can include generally rigid spars 98A and 98B connected with locking hubs 99. With the collapsible frame 94 fully opened, flexible flood source 92 will be retained in a planar orientation as shown. Collapsible frame 94 can alternately be made up of sections which expand and contract by screws, interlocking parts, or telescoping sections in order to apply tension to the flexible flood source in the expanded configuration. The frame 94 is adapted to have a fully opened configuration with a larger form factor, and a collapsed configuration with a smaller form factor.

Figure 13:
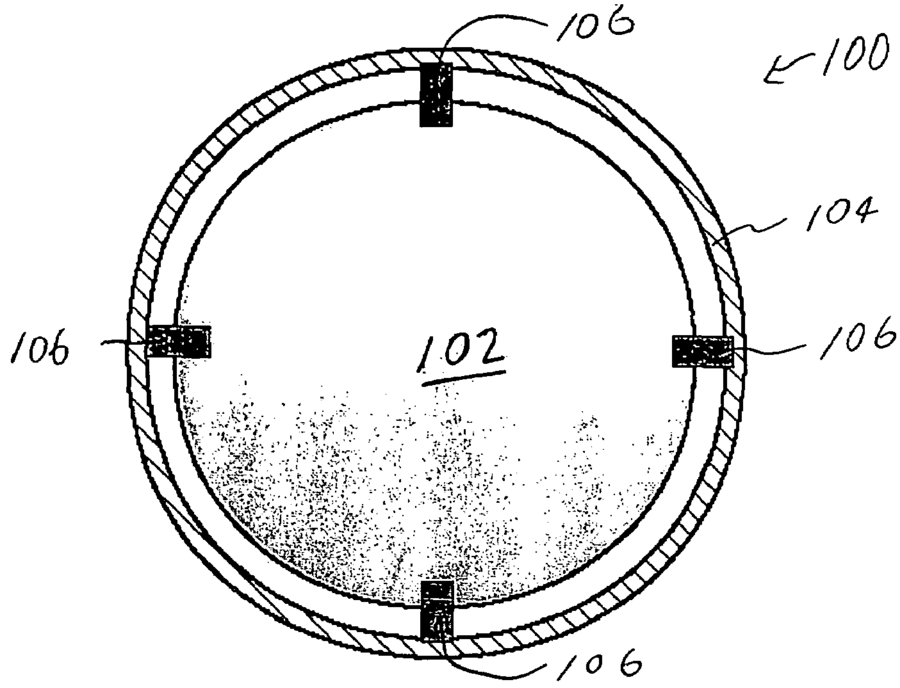
FIG. 13 is a top plan view of another exemplary flexible flood source and an its exemplary compression spring frame, with the flexible flood source attached thereto so that the flexible flood source is extended to a flat orientation.

FIG. 13 is a top plan view of an exemplary embodiment of another flexible flood source exemplary compression spring frame arrangement 100, with an exemplary flexible flood source 102 being attached to a flexible device such as a compression spring frame 104 with attachments 106 (e.g. straps, clips, etc.) thereto which holds the flexible flood source in a flat configuration by means of applied tension so that the flexible flood source is retained in a planar orientation. Other tensioning means can be used.

With respect to all of the embodiments of the flexible flood sources described herein, the flexible encapsulation may be made entirely of a material which is reasonably translucent to gamma radiation, such as fabrics or flexible plastic or flexible coating; or it they be coated or impregnated with regions of radiopaque material. The regions of radiopaque material may be at the edges of the source, to reduce the radiation field to the handler, or they may be in patterns on the face of the source, such as bars or circles, for use in quality control measurements of the camera such as resolution and response to various activity levels. Furthermore, one side of the flexible encapsulation may be made to be radiopaque over the entire face of the source, for applications in which it is only necessary for one face of the source to emit radiation. The configuration of the radiopaque regions includes but is not limited to any of the above configurations and combinations thereof.

The flexible flood source may be provided with a shielded storage case consisting of a container with a compact geometric form factor such as a cylinder or a box with two short dimensions and one long dimension. The shielded storage container should have at least one layer of a high-density, high-atomic-number material that will act to block radiation leakage. The shielded storage container is designed and intended for routine storage of the source by the user during the working life of the source as well as for shipping. The shielded storage case can also be formed of a material that incorporates at least one high-density, high-atomic-number material.

Figure 14:
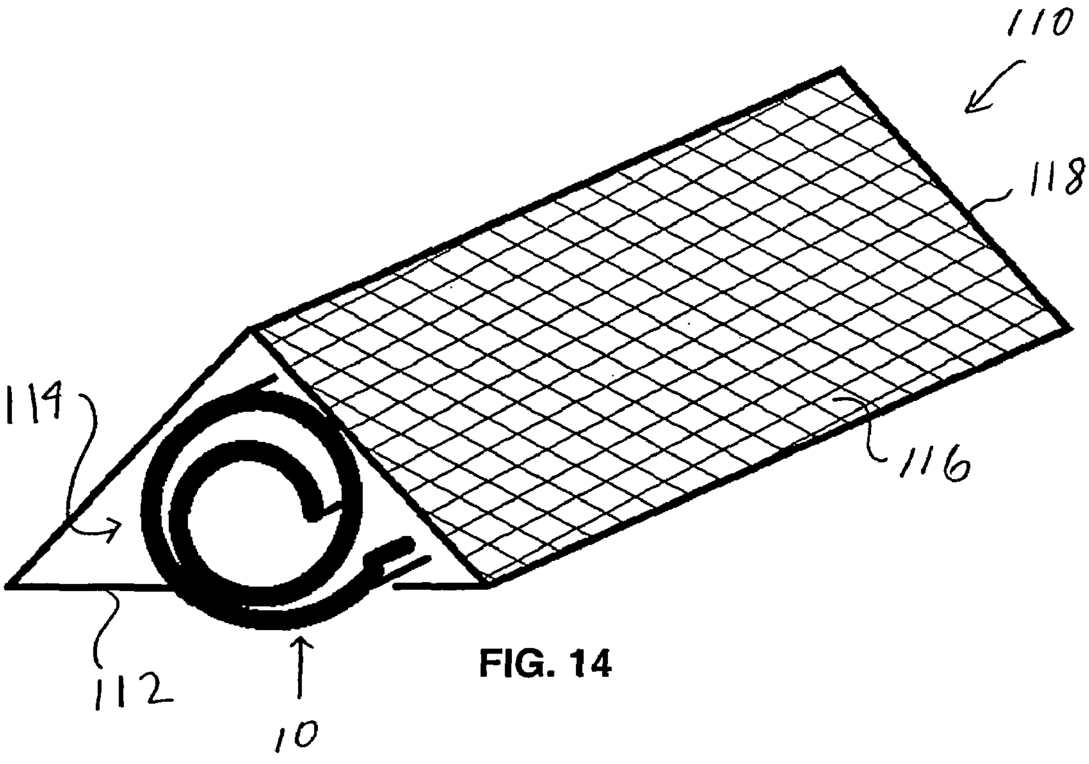
FIG. 14 is a perspective view of an exemplary embodiment of a compact storage and shielding container of the invention shown with an end open and with a rolled up flood source placed inside.

FIG. 14 is a perspective view of an exemplary embodiment of a compact storage and shielding container 110 of the invention with the rolled up exemplary flexible flood source 10 of FIG. 3 inserted through an opening 112 which leads into a cavity 114 formed therein. Compact storage and shielding container 110 has a generally triangular cross section with three side walls 116 and an optionally removable end wall or end closure 118. In use, a removable end cap or other closure (not shown) will be used to close opening 112.

Figure 15:
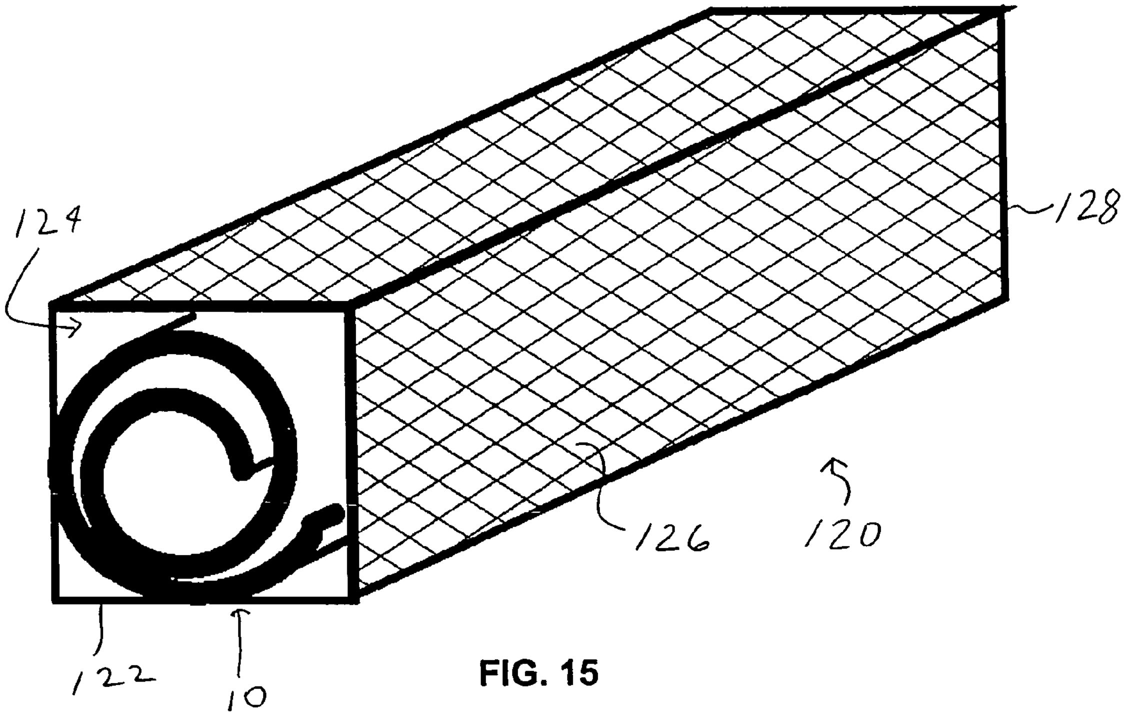
FIG. 15 is a perspective view of another exemplary embodiment of a compact storage and shielding container of the invention shown with an end open and with a rolled up flood source placed inside.

FIG. 15 is a perspective view of another exemplary embodiment of a compact storage and shielding container 120 of the invention with the rolled up exemplary flexible flood source 10 of FIG. 3 inserted through an opening 122 which leads into a cavity 124 formed therein. Compact storage and shielding container 120 has a generally rectangular cross section with four side walls 126 and an optionally removable end wall, end cap or closure 128 that forms a generally parallelepiped shape. In use, a removable end cap or closure (not shown) will be used to close off opening 122.

Figure 16:
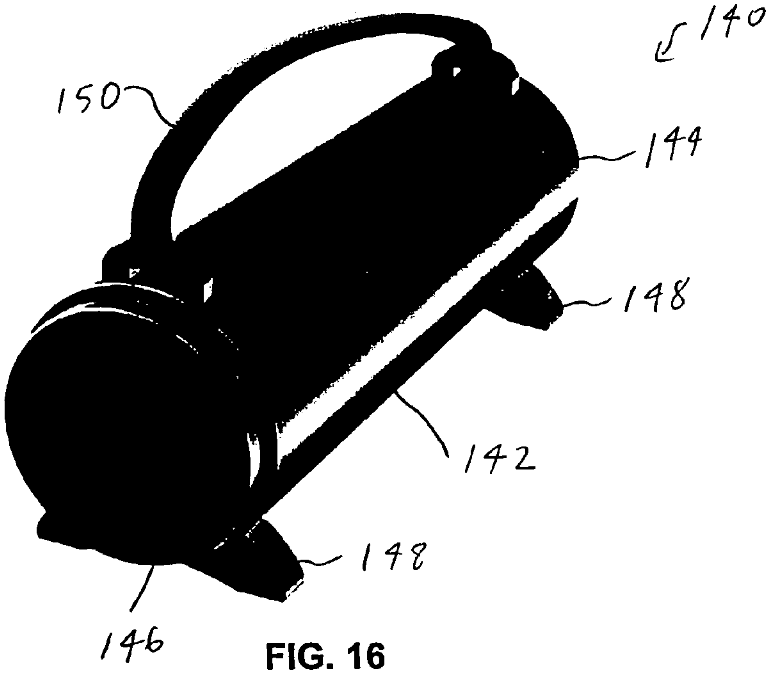
FIG. 16 is a perspective view of a further exemplary embodiment of a compact storage and shielding container of the invention.

FIG. 16 is a perspective view of a further exemplary embodiment of a compact storage and shielding container 140 of the invention, which can have a generally cylindrical storage portion 142, a stationary end cap 144, a removable end cap 146, optional stabilizing legs 148 provided to prevent the compact storage and shielding container 140 from rolling, and a carrying handle 150. The storage portion can have a generally semi-cylindrical or generally oval shape or other desired shapes FIG. 17 is a perspective view of another exemplary compact storage and shielding container 160 of the invention, which has a generally cylindrical storage portion 162, a first removable end cap 164, a second removable end cap 166, optional stabilizing legs 168 so that the compact storage and shielding container 140 will not roll, and a carrying strap 170.

Figure 18:
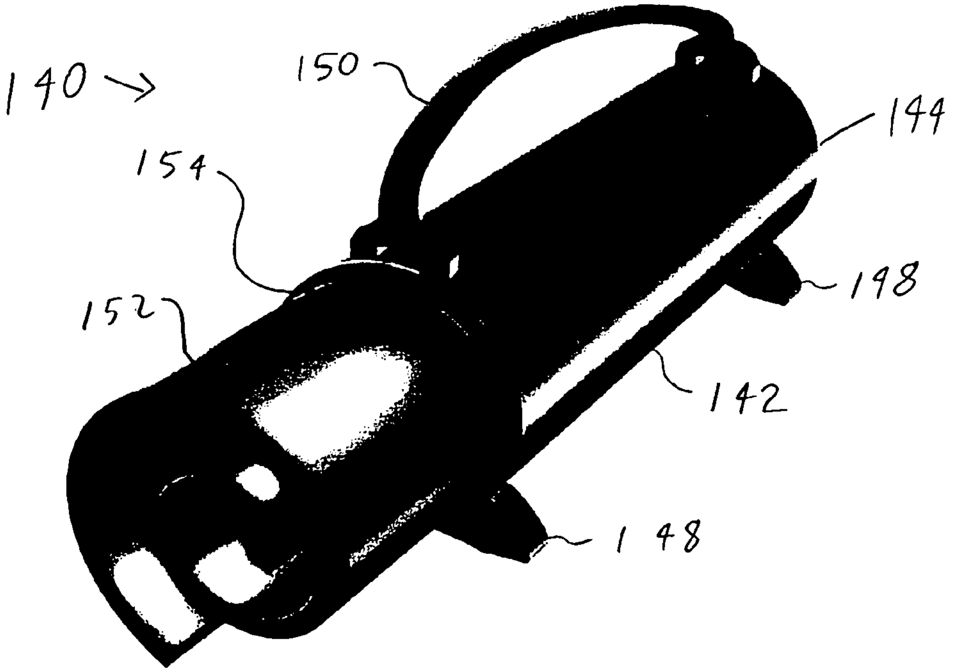
FIG. 18 is a perspective view of the exemplary compact storage and shielding container of FIG. 16, but with its end removed and an exemplary flood source extending therefrom.

FIG. 18 is a perspective view of the exemplary compact storage and shielding container 140 of FIG. 16, but with its end cap removed and with rolled up exemplary flood source 152 extending from the open mouth 154.

Figure 17:
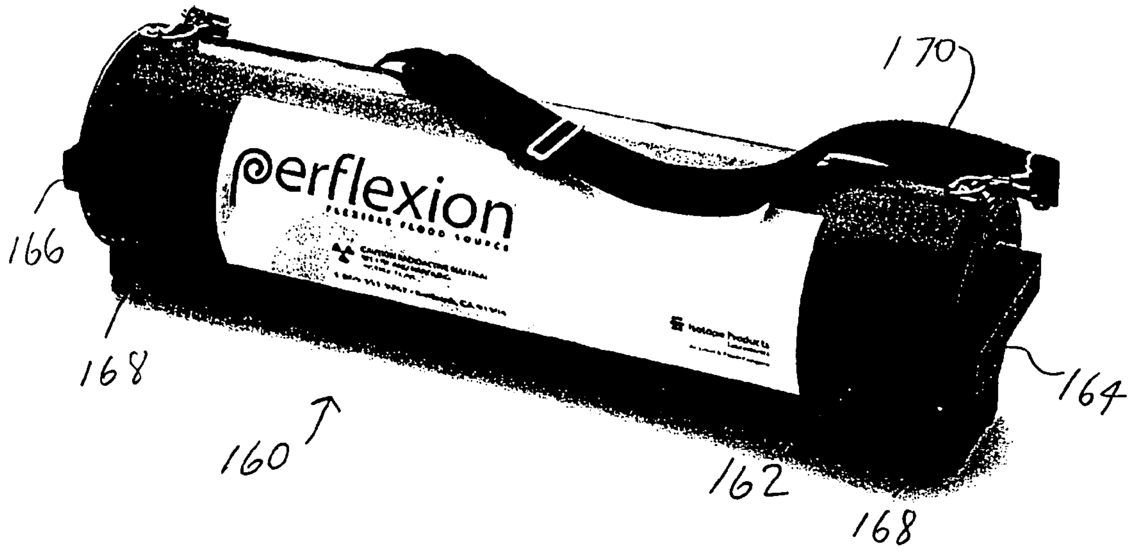
FIG. 17 is a perspective view of yet another exemplary compact storage and shielding container.
Figure 19:
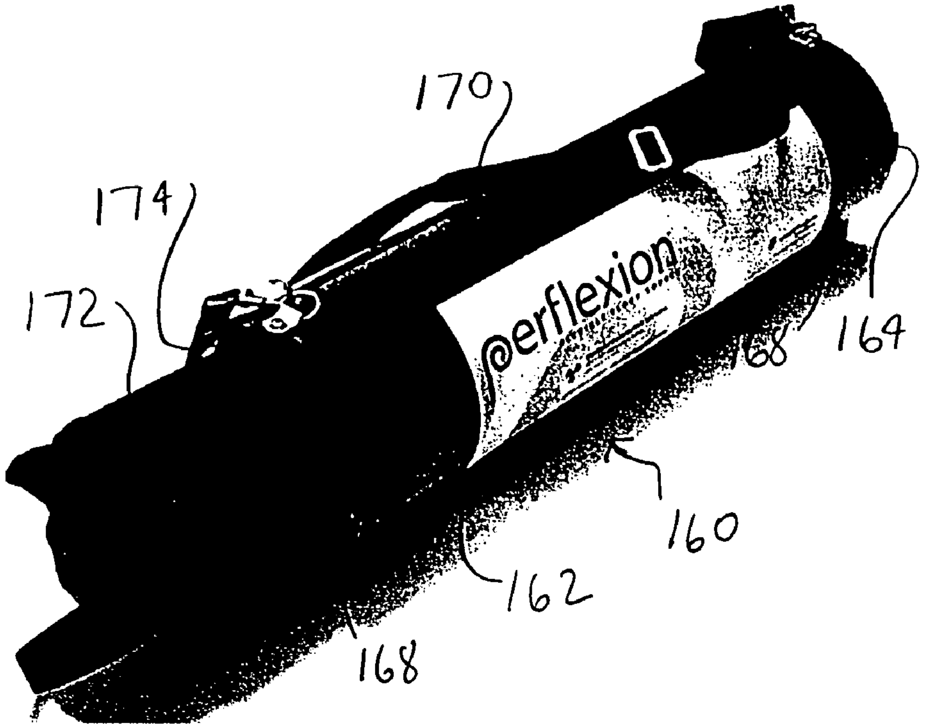
FIG. 19 is a perspective view of the exemplary compact storage and shielding container of FIG. 17, but with its end removed and an exemplary flood source extending therefrom.

FIG. 19 is a perspective view of the exemplary compact storage and shielding container 160 of FIG. 17, but with its second end cap removed and with rolled up exemplary flood source 172 extending from the open mouth 174. Generally cylindrical embodiments of compact storage and shielding containers, such as shown in FIGS. 17–19 provide one preferred geometry of the flood source case, since they have the smallest form factor for a given compact configuration of the flexible flood source. Other designs, such as cylinders with flattened bottoms (to prevent rolling), or even oval designs will also provide efficient container shapes.

Figure 20:
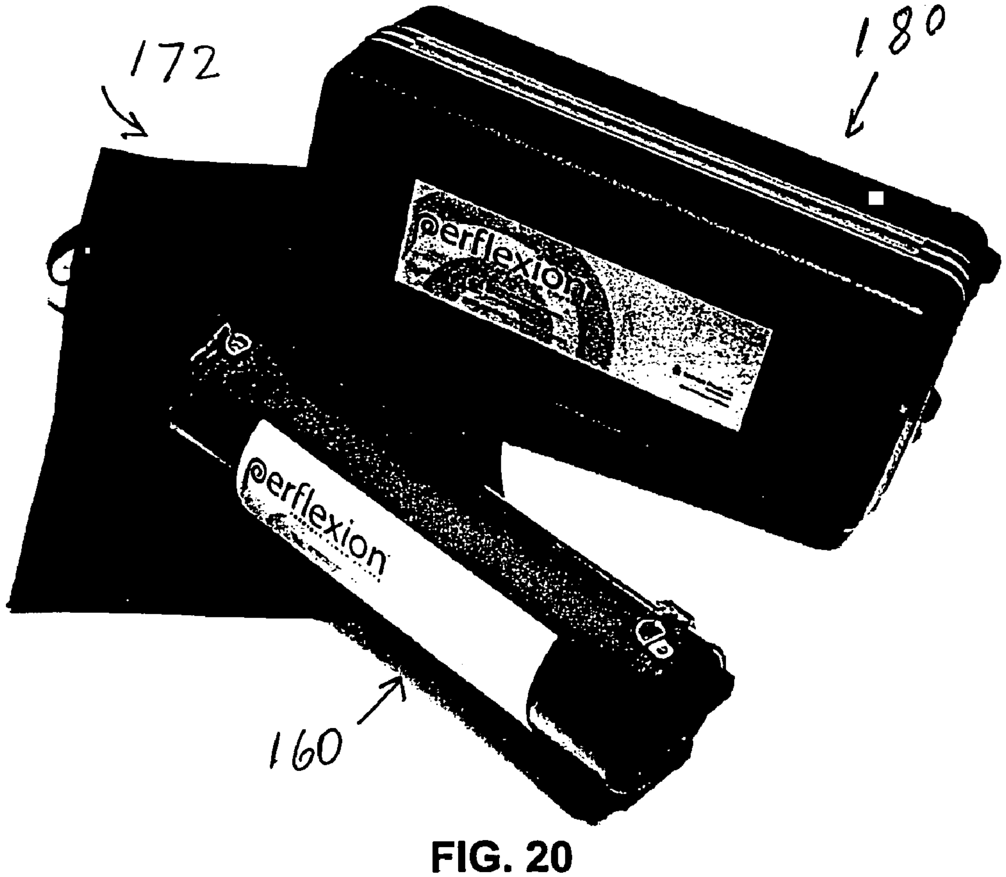
FIG. 20 is a perspective view showing the exemplary compact storage and shielding container of FIG. 17, another exemplary compact storage and shielding container, and an exemplary embodiment of a flexible flood source of the invention.

FIG. 20 is a perspective view showing the exemplary compact storage and shielding container 160 of FIG. 17, another exemplary compact storage and shielding container 180 having a generally parallelepiped or suitcase type of shape, and the exemplary flexible flood source 172 shown in FIG. 19.

Figure 21:
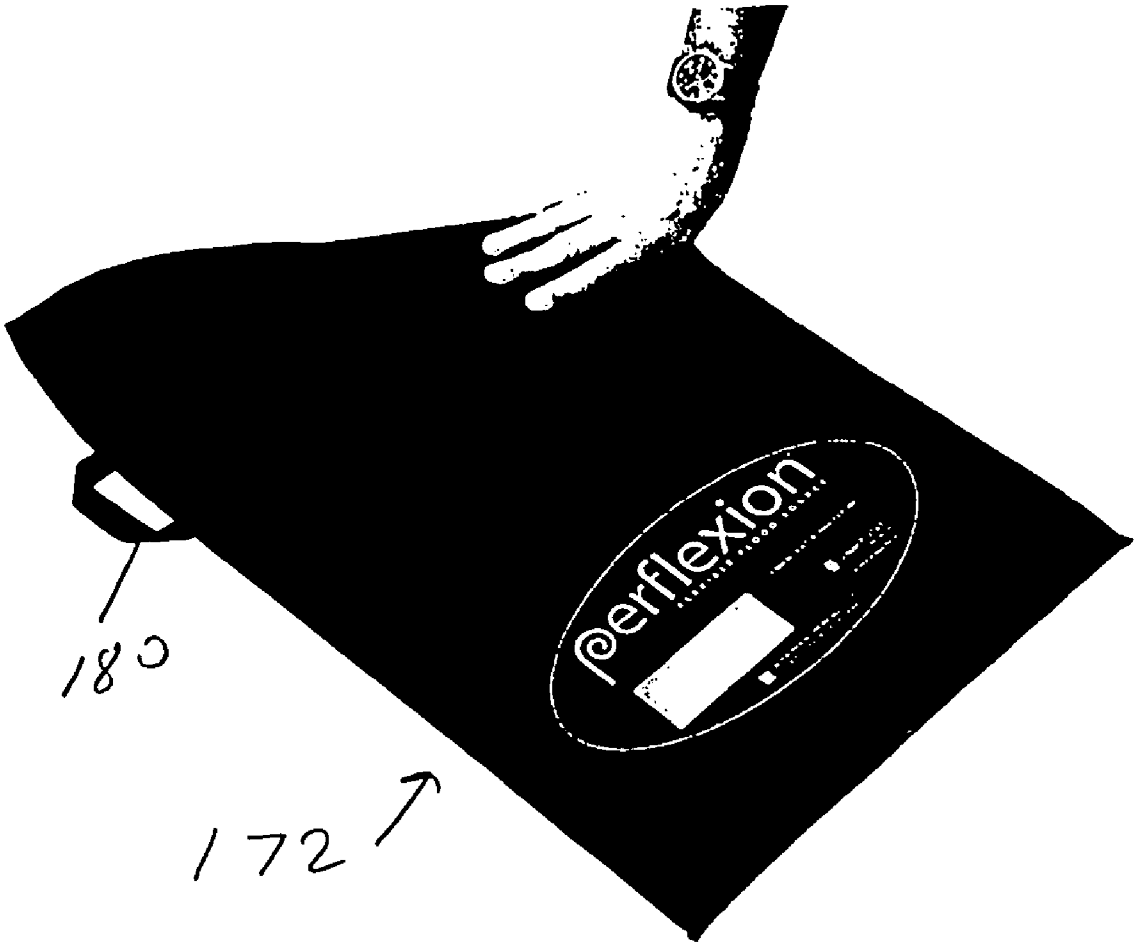
FIG. 21 is a perspective view showing the exemplary flexible flood source of FIG. 20 being flexed.

FIG. 21 is a perspective view showing the exemplary flexible flood source 172 of FIG. 20 being flexed. As can be seen, flexible flood source 172 can have a gripping handle 180 formed thereon.

Although the exemplary compact storage and shielding containers of FIG. 14 and FIGS. 15 and 20 show generally prism-shaped and parallelepiped-shaped containers, respectively, containers having other polygonal ends can be used, with it being preferable that the container is basically a box with two short dimensions (defining the size of the container ends, or with generally circular-shaped ends) and one long dimension (defining the container's width) designed to receive a rolled or folded flood source that has been rolled up along its length to result in the most compact size.

The inner dimensions of the compact storage and shielding containers may have a diameter from about 1.3 cm (0.5") or less to about 20.3 cm (8") or greater (shorter dimension or dimensions) and from about 12.7 cm (5") to about 91.4 cm (36") length (longer dimension) and will be shielded with a high-density, high-atomic-number material. The high-density, high-atomic-number material may consist of but is not limited to lead, tungsten, bismuth, copper, cobalt, gold, nickel, silver, tantalum, and alloys, compounds, composites based on these materials, and combinations thereof; with tungsten and tungsten-based alloys, compounds, and composites being the most favorable choice; and lead and lead-based alloys, compounds, and composites being the second most favorable choice.

The compact storage and shielding containers may also be constructed entirely from the high-density, high-atomic-number material (with common-sense exceptions of hinges, latches, handles, pins, and other accessory hardware); or, it may be built of a structural material such as aluminum, plastic, or wood, with a lining of at least one layer of the high-density, high-atomic-number material; or, the at least one layer of high-density, high-atomic-number material may be sandwiched between one or more layers of structural material such as aluminum, plastic, or wood. The thickness of the high-density, high-atomic-number material shall be sufficient to provide adequate shielding protection when the flexible source is placed inside the case. A typical shielded storage case with cylindrical configuration of about 12.7 cm (5") or less inner diameter and about 50.8 cm (20") or more inside length, and containing a tungsten or tungsten-based composite shielding layer of thickness 1 mm to 3 mm would have external field of approximately 0.1 mR/hour per mCi or less for Co-57 sources, with a typical maximum acceptable external field of 0.3 mR/hour per mCi of Co-57. For other radionuclides and source activity ranges the shielding thickness shall be appropriate for the radiation energy and source activity.

Although the invention has been shown and presented herein by means of certain embodiments of the flexible radiation sources and compact storage and shielding containers therefor, it is to be understood that the invention is not limited thereto but may be variously embodied within the spirit and scope of the invention. Those of ordinary skill in the art will be able to identify various modifications which still remain within the scope of the invention.

We claim:

1. A flexible radiation source, comprising at least one radionuclide dispersed throughout and permanently incorporated into a flexible matrix material, wherein the flexible radiation source can be folded or rolled from an extended or planar configuration to a folded or rolled configuration without causing the at least one radionuclide from becoming separated from the flexible radiation source.

2. The flexible radiation source of claim 1, wherein the flexible matrix material is selected from at least one of the group consisting of an epoxy, a urethane, a silicone, a rubber, a flexible plastic, a cellulose, a polymer gel, and a flexible metal sheet.

3. The flexible radiation source of claim 1, wherein the at least one radionuclide is selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

4. The flexible radiation source of claim 1, wherein the at least one radionuclide is selected from the group consisting of Ba-133, Co-57, Ge-68, Na-22, Gd-153, Cs-137, and Se-75.

5. The flexible radiation source of claim 1, wherein the at least one radionuclide has a level of radioactivity in the range of about 10 nanocuries to about 100 millicuries.

6. The flexible radiation source of claim 1, wherein the at least one radionuclide is uniformly distributed throughout the flexible matrix material.

7. The flexible radiation source of claim 1, wherein the at least one radionuclide is non-uniformly distributed through portions of the flexible matrix material to provide for a region of radioactivity and a region of nonradioactivity or lower radioactivity.

8. The flexible radiation source of claim 7, wherein the region of nonradioactivity or lower radioactivity comprises a border area around an edge of the flexible radiation source.

9. The flexible radiation source of claim 7, wherein the region of nonradioactivity or lower radioactivity is in the form of a geometric pattern within a body of the flexible radiation source.

10. The flexible radiation source of claim 7, wherein the region of radioactivity is in the form of a geometric pattern within a non-radioactive body of the flexible radiation source.

11. The flexible radiation source of claim 1, wherein the flexible radiation source has a generally rectangular shape with minimum dimensions of about 12.7 cm×12.7 cm, and maximum dimensions of about 76 cm×76 cm.

12. The flexible radiation source of claim 1, wherein the flexible radiation source has a circular shape with a minimum diameter of about 12.7 cm and a maximum diameter of about 76 cm.

13. The flexible radiation source of claim 1, wherein the flexible radiation source has a minimum thickness of about 0.4 mm and a maximum thickness of about 3.8 cm.

14. The flexible radiation source of claim 1, wherein the flexible radiation source has a minimum weight of about 40 g and a maximum weight of about 3.6 kg.

15. The flexible radiation source of claim 1, wherein the flexible radiation source lies flat when placed on a flat surface.

16. The flexible radiation source of claim 1, wherein the flexible radiation source comprises a flexible memory material that will generally assume the geometry in which the flexible radiation source was manufactured.

17. The flexible radiation source of claim 1, wherein the at least one radionuclide is dispersed throughout and permanently incorporated into the flexible matrix material by physical suspension.

18. The flexible radiation source of claim 1, wherein the radionuclide is dispersed throughout and permanently incorporated into the flexible matrix material by chemical dissolution.

19. The flexible radiation source of claim 1, wherein the flexible radiation source is free from encapsulation by any rigid structure.

20. The flexible radiation source of claim 1, wherein the flexible nonradioactive material further comprises radiopaque material.

21. The flexible radiation source of claim 20, wherein the radiopaque material comprises an element or composite material with a density greater than 5 g/cc.

22. The flexible radiation source of claim 20, wherein the radiopaque material is selected from the group consisting of at least one of lead, tungsten, bismuth, copper, cobalt, gold, nickel, silver, tantalum, and alloys, compounds, composites based on these materials, and combinations thereof.

23. The flexible radiation source of claim 20, wherein the radiopaque material is provided in the form of geometric patterns.

24. The flexible radiation source of claim 20, wherein the radiopaque material comprises at least 10% by weight of at least one element with an atomic number greater than 20.

25. The flexible radiation source of claim 20, wherein the radiopaque material comprises at least 10% by weight of at least one of lead, tungsten, tantalum, bismuth, uranium, and combinations thereof.

26. The flexible radiation source of claim 1, wherein the flexible radiation source further comprises a support structure which assists the flexible source in maintaining a flat geometry.

27. The flexible radiation source of claim 26, wherein the support structure is permanently attached to or incorporated to the flexible matrix material.

28. The flexible radiation source of claim 26, wherein the support structure comprises a support plate comprising a plurality of segments or slats, which are adapted to connect or interlock to provide a flat, rigid support configuration, and which, when not connected or interlocked permit the support plate to be flexed, rolled, or folded.

29. The flexible radiation source of claim 28, wherein the segments or slats are made such that when the support plate is in its support configuration, the support plate has generally uniform transparency to radiation over a surface which supports the flexible matrix material.

30. The flexible radiation source of claim 28, wherein the segments or slats have areas of differing transparency to radiation, or radiopaque properties.

31. The flexible radiation source of claim 28, wherein the support plate is made of a lightweight, low-atomic-number material.

32. The flexible radiation source of claim 28, wherein the support plate is made of a material selected from the group consisting of thermoplastic, epoxy resin, fiberglass, wood or wood-fiber products, carbon-fiber, and composites thereof.

33. The flexible radiation source of claim 26, wherein the support structure comprises a frame which attaches to an edge of the flexible matrix material.

34. The flexible radiation source of claim 33, wherein the frame is provided with additional supports that extend across a face of the flexible matrix material.

35. The flexible radiation source of claim 33, wherein the frame is adapted to have a fully opened configuration with a larger form factor, and a collapsed configuration with a smaller form factor.

36. The flexible radiation source of claim 33, wherein the frame is selected from the group consisting of at least one of interlocking segments, joints, telescoping segments, and segments that are fully disassembled from one another.

37. The flexible radiation source of claim 33, wherein the frame includes a spring which tensions the flexible matrix material.

38. The flexible radiation source of claim 1, wherein the flexible radiation source is provided with a storage and shielding container with a compact form factor.

39. The flexible radiation source of claim 38, wherein the storage and shielding container includes at least one layer of a high-density, high-atomic-number material.

40. The flexible radiation source of claim 39, wherein the high-density, high-atomic-number material is selected from the group consisting of lead, tungsten, bismuth, copper, cobalt, gold, nickel, silver, tantalum, and alloys, compounds, composites based on these materials, and combinations thereof.

41. The flexible radiation source of claim 1, wherein the form factor of the storage and shielding container accommodates the flexible radiation source when the flexible radiation source is in its rolled or folded configuration, but does not accommodate the flexible radiation source when it is in fully extended or planar configuration.

42. The flexible radiation source of claim 38, wherein the storage and shielding container is constructed from a material that incorporates high-density, high-atomic-number material.

43. The flexible radiation source of claim 42, wherein the high-density, high-atomic-number material is selected from the group consisting of lead, tungsten, bismuth, copper, cobalt, gold, nickel, silver, tantalum, and alloys, compounds, composites based on these materials, and combinations thereof.

44. The flexible radiation source of claim 38, wherein the storage and shielding container has a generally cylindrical, generally semi-cylindrical, or generally oval shape.

45. The flexible radiation source of claim 38, wherein the storage and shielding container has a generally parallelepiped or prism shape.

46. The flexible radiation source of claim 38, wherein the storage and shielding container has a minimum shortest inner dimension of about 2.5 cm, and a maximum longest inner dimension of about 92 cm.

47. A flexible radiation source, comprising:

a layer of flexible material with at least one radionuclide dispersed therein to form a flexible, radioactive matrix, and a layer of flexible nonradioactive material, wherein the flexible radiation source can be folded or rolled from an extended or planar configuration to a folded or rolled configuration without causing the at least one radionuclide from becoming separated from the flexible radiation source.

48. The flexible radiation source of claim 47, wherein the flexible, radioactive matrix and the layer of flexible nonradioactive material are selected from at least one of the group consisting of an epoxy, a urethane, a silicone, a rubber, a flexible plastic, a cellulose, a polymer gel, and a flexible metal sheet.

49. The flexible radiation source of claim 47, wherein the at least one radionuclide is selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

50. The flexible radiation source of claim 47, wherein the at least one radionuclide is selected from the group consisting of Ba-133, Co-57, Ge-68, Na-22, Gd-153, Cs-137, and Se-75.

51. The flexible radiation source of claim 47, wherein the at least one radionuclide has a level of radioactivity in the range of about 10 nanocuries to about 100 millicuries.

52. The flexible radiation source of claim 47, wherein the at least one radionuclide is uniformly distributed throughout the flexible, radioactive matrix.

53. The flexible radiation source of claim 47, wherein the at least one radionuclide is distributed through portions of the flexible, radioactive matrix to provide for a region of radioactivity and a region of nonradioactivity or lower radioactivity.

54. The flexible radiation source of claim 47, wherein the region of nonradioactivity or lower radioactivity comprises a border area around an edge of the flexible radiation source.

55. The flexible radiation source of claim 47, wherein the region of nonradioactivity or lower radioactivity is in the form of a geometric pattern within a body of the flexible radioactive matrix.

56. The flexible radiation source of claim 47, wherein the region of radioactivity is in the form of a geometric pattern within a non-radioactive body of the flexible radioactive matrix.

57. The flexible radiation source of claim 47, wherein the flexible radiation source has a generally rectangular shape with minimum dimensions of about 12.7 cm×12.7 cm, and maximum dimensions of about 76 cm×76 cm.

58. The flexible radiation source of claim 47, wherein the flexible radiation source has a circular shape with a minimum diameter of about 12.7 cm and a maximum diameter of about 76 cm.

59. The flexible radiation source of claim 47, wherein the flexible radiation source has a minimum thickness of about 0.4 mm and a maximum thickness of about 3.8 cm.

60. The flexible radiation source of claim 47, wherein the flexible radiation source has a minimum weight of about 40 g and a maximum weight of about 3.6 kg.

61. The flexible radiation source of claim 47, wherein the flexible radiation source lies flat when placed on a flat surface.

62. The flexible radiation source of claim 47, wherein the flexible radiation source comprises a flexible memory material that will generally assume the geometry in which the flexible radiation source was manufactured.

63. The flexible radiation source of claim 47, wherein the at least one radionuclide is dispersed throughout and permanently incorporated into the flexible, radioactive matrix material by physical suspension.

64. The flexible radiation source of claim 47, wherein the radionuclide is dispersed throughout and permanently incorporated into the flexible matrix material by chemical dissolution.

65. The flexible radiation source of claim 47, wherein the flexible radiation source is free from encapsulation by any rigid structure.

66. The flexible radiation source of claim 47, wherein the layer of flexible, radioactive matrix and the flexible nonradioactive material are permanently bound or attached together.

67. The flexible radiation source of claim 47, wherein the layer of flexible, radioactive matrix and the flexible nonradioactive material are permanently bound or attached together by at least one of the group consisting of adhesive, mechanical fasteners, and one of the flexible, radioactive matrix and the flexible nonradioactive material being coated onto the other.

68. The flexible radiation source of claim 47, wherein the layer of flexible nonradioactive material envelops the flexible, radioactive matrix.

69. The flexible radiation source of claim 68, wherein the layer of flexible nonradioactive material that envelops the flexible, radioactive matrix is not bound or attached to the flexible, radioactive matrix.

70. The flexible radiation source of claim 68, wherein the layer of flexible nonradioactive material that envelops the flexible, radioactive matrix is not permanently bound or attached to the flexible, radioactive matrix.

71. The flexible radiation source of claim 68, wherein the layer of flexible nonradioactive material that envelops the flexible, radioactive matrix comprises at least one of a natural or synthetic cloth, a flexible polymer, and paper.

72. The flexible radiation source of claim 47, wherein the flexible, radioactive matrix, and the layer of flexible nonradioactive material are made of the same material.

73. The flexible radiation source of claim 68, wherein the layer of flexible nonradioactive material that envelops the flexible, radioactive matrix is permanently sealed shut by at least one of the group consisting of sewing, adhesive bonding, and chemically or physically fusing together of the layer of flexible nonradioactive material.

74. The flexible radiation source of claim 68, wherein the layer of flexible nonradioactive material that envelops the flexible, radioactive matrix is provided with a closure that may be opened so that the flexible, radioactive matrix may be removed.

75. The flexible radiation source of claim 47, wherein the flexible nonradioactive material further comprises radiopaque material.

76. The flexible radiation source of claim 75, wherein the radiopaque material is provided in the form of geometric patterns.

77. The flexible radiation source of claim 75, wherein the radiopaque material comprises an element or composite material with a density greater than 5 g/cc.

78. The flexible radiation source of claim 75, wherein the radiopaque material is selected from the group consisting of at least one of lead, tungsten, bismuth, copper, cobalt, gold, nickel, silver, tantalum, and alloys, compounds, composites based on these materials, and combinations thereof.

79. The flexible radiation source of claim 75, wherein the radiopaque material comprises at least 10% by weight of at least one element with an atomic number greater than 20.

80. The flexible radiation source of claim 75, wherein the radiopaque material comprises at least 10% by weight of at least one lead, tungsten, tantalum, bismuth, uranium, and combinations thereof.

81. The flexible radiation source of claim 47, wherein the flexible source is provided with a support structure which assists the flexible radiation source in maintaining a flat geometry.

82. The flexible radiation source of claim 81, wherein the support structure is permanently attached to or incorporated to the flexible matrix material.

83. The flexible radiation source of claim 81, wherein the support structure comprises a support plate comprising a plurality of segments or slats, which are adapted to connect or interlock to provide a flat, rigid support configuration, and which, when not connected or interlocked permit the support plate to be flexed, rolled, or folded.

84. The flexible radiation source of claim 83, wherein the segments or slats are made such that when the support plate is in its support configuration, the support plate has generally uniform transparency to radiation over a surface which supports the flexible matrix material.

85. The flexible radiation source of claim 83, wherein the segments or slats have areas of differing transparency to radiation, or radiopaque properties.

86. The flexible radiation source of claim 83, wherein the support plate is made of a lightweight, low-atomic-number material.

87. The flexible radiation source of claim 83, wherein the support plate is made of a material selected from the group consisting of thermoplastic, epoxy resin, fiberglass, wood or wood-fiber products, carbon-fiber, and composites thereof.

88. The flexible radiation source of claim 81, wherein the support structure comprises a frame which attaches to an edge of the layer of non-radioactive material.

89. The flexible radiation source of claim 88, wherein the frame is provided with additional supports that extend across a face of the flexible matrix material.

90. The flexible radiation source of claim 88, wherein the frame is adapted to have a fully opened configuration with a larger form factor, and a collapsed configuration with a smaller form factor.

91. The flexible radiation source of claim 88, wherein the frame is selected from the group consisting of at least one of interlocking segments, joints, telescoping segments and segments that are fully disassembled from one another.

92. The flexible radiation source of claim 88, wherein the frame includes a spring which tensions the flexible matrix material.

93. The flexible radiation source of claim 47, wherein the flexible radiation source is provided with a storage and shielding container with a compact form factor.

94. The flexible radiation source of claim 93, wherein the form factor of the storage and shielding container accommodates the flexible radiation source when the flexible radiation source is in its rolled or folded configuration, but does not accommodate the flexible radiation source when it is in fully extended or planar configuration.

95. The flexible radiation source of claim 93, wherein the storage and shielding container includes at least one layer of a high-density, high-atomic-number material.

96. The flexible radiation source of claim 93, wherein the storage and shielding container is constructed from a material that incorporates high-density, high-atomic-number material.

97. The flexible radiation source of claim 95, the high-density, high-atomic-number material is selected from the group consisting of lead, tungsten, bismuth, copper, cobalt, gold, nickel, silver, tantalum, and alloys, compounds, composites based on these materials, and combinations thereof.

98. The flexible radiation source of claim 96, the high-density, high-atomic-number material is selected from the group consisting of lead, tungsten, bismuth, copper, cobalt, gold, nickel, silver, tantalum, and alloys, compounds, composites based on these materials, and combinations thereof.

99. The flexible radiation source of claim 93, wherein the storage and shielding container has a generally cylindrical, generally semi-cylindrical, or generally oval shape.

100. The flexible radiation source of claim 93, wherein the storage and shielding container has a generally parallelepiped or prism shape.

101. A flexible radiation source, comprising at least one radionuclide dispersed throughout and permanently incorporated into a flexible matrix material, wherein the flexible radiation source can be folded or rolled from an extended or planar configuration to a folded or rolled configuration without causing the at least one radionuclide from becoming separated from the flexible radiation source, and which flexible matrix material is free from encapsulation by any rigid structure.

102. The flexible radiation source of claim 101, wherein the flexible radiation source is provided with a storage and shielding container with a compact form factor, wherein the form factor of the storage and shielding container accommodates the flexible radiation source when the flexible radiation source is in its rolled or folded configuration, but does not accommodate the flexible radiation source when it is in fully extended or planar configuration.

103. The flexible radiation source of claim 101, wherein the at least one radionuclide is selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, and has a level of radioactivity in the range of about 10 nanocuries to about 100 millicuries.

104. A flexible radiation source, comprising:

a layer of flexible material with at least one radionuclide dispersed therein to form a flexible, radioactive matrix, and a layer of flexible nonradioactive material to which the flexible, radioactive matrix is permanently attached, wherein the flexible radiation source can be folded or rolled from an extended or planar configuration to a folded or rolled configuration without causing the at least one radionuclide from becoming separated from the flexible radiation source, and which flexible matrix material is free from encapsulation by any rigid structure.

105. The flexible radiation source of claim 104, wherein the layer of flexible nonradioactive material envelops the flexible, radioactive matrix.

106. The flexible radiation source of claim 104, further comprising a storage and shielding container with a compact form factor, wherein the form factor of the storage and shielding container accommodates the flexible radiation source when the flexible radiation source is in its rolled or folded configuration, but does not accommodate the flexible radiation source when it is in fully extended or planar configuration.

107. The flexible radiation source of claim 104, wherein the at least one radionuclide is selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, and has a level of radioactivity in the range of about 10 nanocuries to about 100 millicuries.

* * * * *